(12) United States Patent
Hibi et al.

(10) Patent No.: US 8,701,035 B2
(45) Date of Patent: Apr. 15, 2014

(54) INDEX IMAGE CONTROL APPARATUS

(75) Inventors: Yasushi Hibi, Machida (JP); Yoshiyuki Okuno, Fussa (JP)

(73) Assignee: Olympus Medical Systems Corp., Tokyo (JP)

( * ) Notice: Subject to any disclaimer, the term of this patent is extended or adjusted under 35 U.S.C. 154(b) by 507 days.

(21) Appl. No.: 13/042,771

(22) Filed: Mar. 8, 2011

(65) Prior Publication Data

US 2011/0161862 A1      Jun. 30, 2011

Related U.S. Application Data

(63) Continuation of application No. PCT/JP2009/065436, filed on Sep. 3, 2009.

(30) Foreign Application Priority Data

Sep. 9, 2008   (JP) .................................. 2008-231311

(51) Int. Cl.
      *G06F 3/048*           (2013.01)

(52) U.S. Cl.
      USPC ........... 715/781; 715/863; 715/828; 600/424; 600/437; 600/443; 382/128

(58) Field of Classification Search
      USPC .......... 715/863, 781, 828; 600/424, 437, 443; 382/128
      See application file for complete search history.

(56) References Cited

U.S. PATENT DOCUMENTS

| | | | |
|---|---|---|---|
| 5,315,999 A * | 5/1994 | Kinicki et al. ................ | 600/443 |
| 6,077,226 A | 6/2000 | Washburn et al. | |
| 6,333,752 B1 * | 12/2001 | Hasegawa et al. ............ | 715/764 |
| 6,468,212 B1 * | 10/2002 | Scott et al. .................... | 600/437 |
| 6,491,630 B1 * | 12/2002 | Saccardo et al. .............. | 600/437 |
| 7,852,352 B2 * | 12/2010 | Sugiyama et al. ............ | 345/629 |
| 2008/0161688 A1 * | 7/2008 | Poland .......................... | 600/437 |

(Continued)

FOREIGN PATENT DOCUMENTS

| | | |
|---|---|---|
| CN | 101040245 A | 9/2007 |
| EP | 1 942 352 A2 | 7/2008 |

(Continued)

OTHER PUBLICATIONS

Morrow et al.; Region-Based Contrast Enhancement of Mammograms; Sep. 1992, Transactions on Medical Imaging; vol. 11, No. 3; 14 pages.*

(Continued)

*Primary Examiner* — Linh K Pham
*Assistant Examiner* — Tam Tran
(74) *Attorney, Agent, or Firm* — Scully, Scott, Murphy & Presser, P.C.

(57) ABSTRACT

An ultrasound diagnostic apparatus using an index image display apparatus includes: an index image display section for displaying an ROI of an index image having a predetermined shape and to be superimposed on an image displayed on a monitor; a CPU that is a display form changing section that can change a display form of the ROI by a predetermined amount by one operation; an operation portion for outputting an operation signal to the CPU; and an LCD panel that is a change information display section including a plurality of operation buttons provided in the operation portion and representing graphic information that indicates an initial state of the ROI, and change information that is changed by the CPU.

13 Claims, 9 Drawing Sheets

(56) References Cited

U.S. PATENT DOCUMENTS

| | | | |
|---|---|---|---|
| 2008/0221446 A1* | 9/2008 | Washburn et al. | 600/437 |
| 2008/0242983 A1* | 10/2008 | Hibi | 600/441 |
| 2009/0043195 A1* | 2/2009 | Poland | 600/437 |
| 2009/0227872 A1* | 9/2009 | Pan et al. | 600/458 |
| 2010/0030079 A1* | 2/2010 | Hamada | 600/443 |
| 2010/0049046 A1* | 2/2010 | Peiffer et al. | 600/443 |
| 2010/0145195 A1* | 6/2010 | Hyun | 600/437 |
| 2011/0113361 A1* | 5/2011 | Bhatt et al. | 715/781 |
| 2011/0152685 A1* | 6/2011 | Misono | 600/443 |
| 2011/0161862 A1* | 6/2011 | Hibi et al. | 715/781 |
| 2012/0310090 A1* | 12/2012 | Miyachi et al. | 600/440 |
| 2013/0024806 A1* | 1/2013 | Funabashi et al. | 715/781 |

FOREIGN PATENT DOCUMENTS

| | | |
|---|---|---|
| JP | 02-197862 | 8/1990 |
| JP | 05-293102 | 11/1993 |
| JP | 06-269453 | 9/1994 |
| JP | 2007-159922 | 6/2007 |
| JP | 2008-515583 A | 5/2008 |
| JP | 2008-245789 | 10/2008 |
| JP | 2009-213796 | 9/2009 |
| SH | Sho 59-20155 | 2/1984 |
| WO | 03/027662 A2 | 4/2003 |
| WO | 2006/038181 | 4/2006 |
| WO | WO 2006/040697 A1 | 4/2006 |
| WO | WO 2008/081558 * | 7/2010 ............... A61B 8/00 |

OTHER PUBLICATIONS

Wein et al.; Integrating Diagnostic B-Mode Ultrasonography Into CT-Based Radiation Treatment Planning; Jun. 2007, Transactions on Medical Imaging; vol. 26, No. 6; 13 pages.*
Abolmaesumi et al.; Image-Guided Control of a Robot for Medical Ultrasound; Feb. 2002; Transactions on Robotics and Automation; vol. 18, No. 1; 12 pages.*
International Search Report dated Oct. 13, 2009.
European Search Report dated Jul. 16, 2013 from corresponding European Application No. 09 81 3035.4.

* cited by examiner

INDEX IMAGE CONTROL APPARATUS

CROSS REFERENCE TO RELATED APPLICATION

This application is a continuation application of PCT/JP2009/065436 filed on Sep. 3, 2009 and claims benefit of Japanese Application No. 2008-231311 filed in Japan on Sep. 9, 2008, the entire contents of which are incorporated herein by this reference.

BACKGROUND OF INVENTION

1. Field of the Invention

The present invention relates to an index image control apparatus, and particularly to an index image control apparatus that can change a display region of an index image to be displayed on a screen of a monitor.

2. Description of the Related Art

In recent years, ultrasound diagnostic apparatuses are widely used in the medical and industrial fields. An ultrasound diagnostic apparatus repeatedly transmits ultrasound from an ultrasound transducer to a biological tissue, and receives an echo signal of ultrasound reflected from the biological tissue to display the information in a living body as a visible ultrasound tomographic image (hereafter, simply referred to as an ultrasound image).

In particular, an electronic scanning type ultrasound diagnostic apparatus, which electronically drives an ultrasound transducer to scan inside a body cavity, makes it possible to freely change the scanning method and to scan in various modes such as a flow mode including a color flow mode that can visualize the image of blood flow, besides a B-mode that displays a normal black-and-white image.

Moreover, an electronic scanning type ultrasound endoscope displays a blood flow image, which is calculated by Doppler processing, on a monitor upon execution of a color flow mode. In this case, a region of interest (hereafter, referred to as an ROI) in which the image of the Doppler processing is displayed is displayed on the display screen of the monitor. It is noted that in the ROI, a blood flow image is displayed in a preset display region as an index image.

Such an ultrasound diagnostic apparatus includes an operation portion for inputting various data and instruction signals. The operation portion is generally made up of a plurality of keys and switches, etc. provided on an operation panel of the ultrasound diagnostic apparatus, or a plurality of keys and switches, a trackball, and the like provided on a keyboard.

An example of conventional art for improving the operability of an ultrasound diagnostic apparatus includes an ultrasound diagnostic apparatus according to Japanese Patent Application Laid-Open Publication 2007-159922.

The ultrasound diagnostic apparatus according to Japanese Patent Application Laid-Open Publication No. 2007-159922 includes a touch panel that is substantially integrally disposed with a display surface of a display section (a monitor), in which an inspection-width setting function activation region is provided on the touch panel and thereby a display to show a function of changing the display width of image is performed so that changing operation of the display width is enabled.

In general, in the observation utilizing an ROI that is displayed during the execution of a color flow mode, the operator used to move the ROI to a desired position by operating a switch such as a trackball etc. provided in an operation portion of the ultrasound diagnostic apparatus, or to change the size of the ROI by operating a plurality of keys, thereby changing the display region of the ROI.

SUMMARY OF THE INVENTION

An index image control apparatus of the present invention includes: an index image display section for displaying an index image having a predetermined shape and to be superimposed on an image displayed on a monitor; a display form changing section that can change a display form of the index image by a predetermined amount by one operation; an operation section for outputting an operation signal to the display form changing section; a change information display section provided in the operation section and representing graphic information that indicates an initial state of the index image, and change information that is changed by the display form changing section.

Moreover, an index image control apparatus of the present invention includes: an index image display section for displaying an index image having a predetermined shape on a monitor; an index image operation section including a plurality of operation buttons that each simultaneously display both graphic information having a shape in an initial state of the index image displayed on the monitor, and change information of at least one of upper, lower, leftward, and rightward directions, the change information changing a display region of the index image displayed on the monitor; and an index image changing section for changing a display region of the index image displayed on the monitor according to the change information on an operation button that is operated in the index image operation section.

DETAILED DESCRIPTION OF THE PREFERRED EMBODIMENT(S)

Hereafter, embodiments of the present invention will be described with reference to the drawings.

Figure 1:
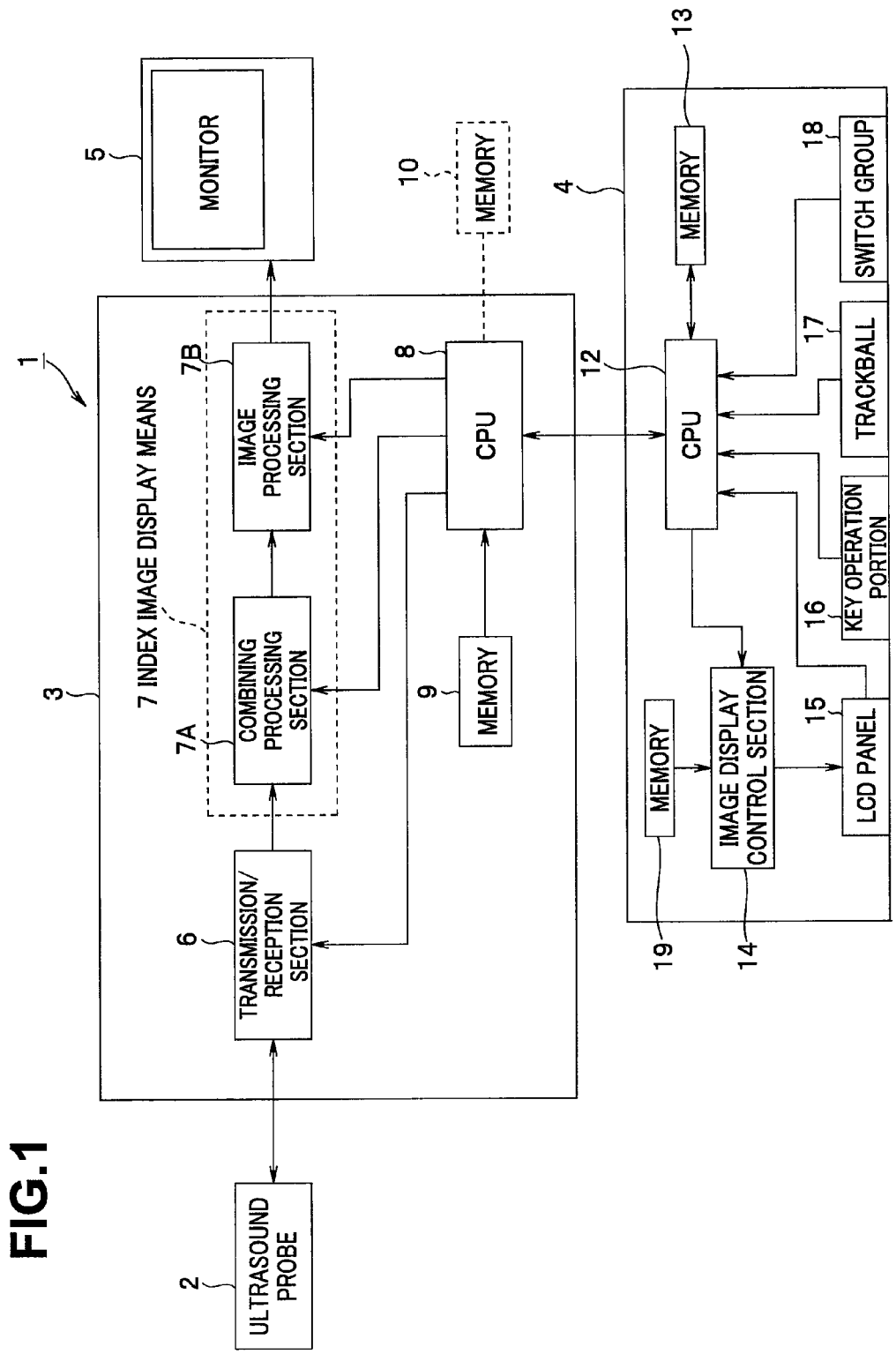
FIG. 1 is a block diagram showing an overall configuration of an ultrasound diagnostic apparatus using an index image control apparatus relating to an embodiment of the present invention.
Figure 2:
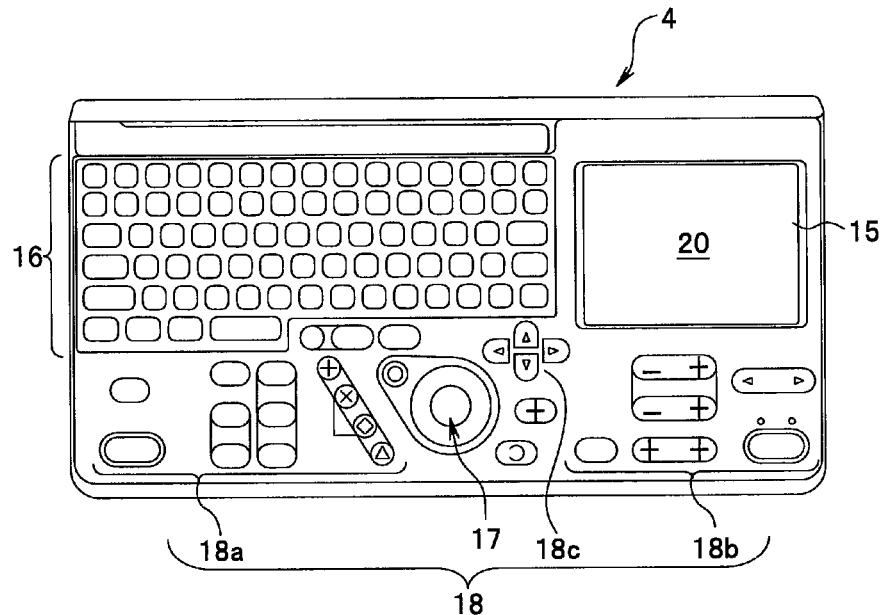
FIG. 2 is a configuration diagram showing a specific configuration of the operation portion of FIG. 1.
Figure 3:
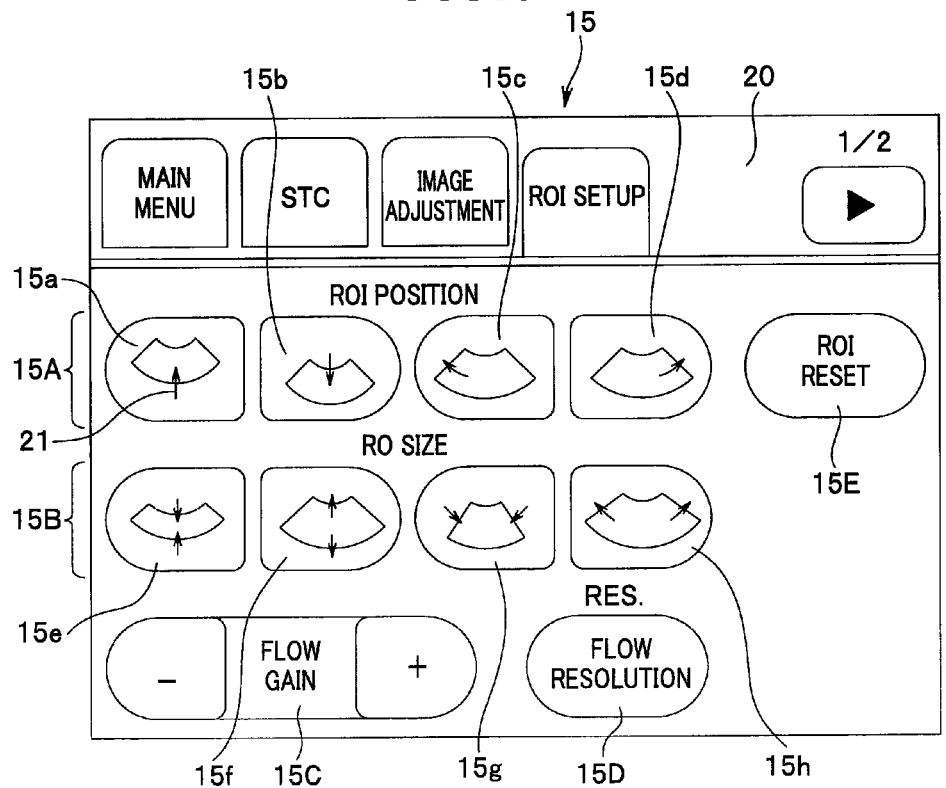
FIG. 3 is a diagram showing a configuration example of an ROI setup operation portion displayed on the LCD panel of FIG. 2.
Figure 4:
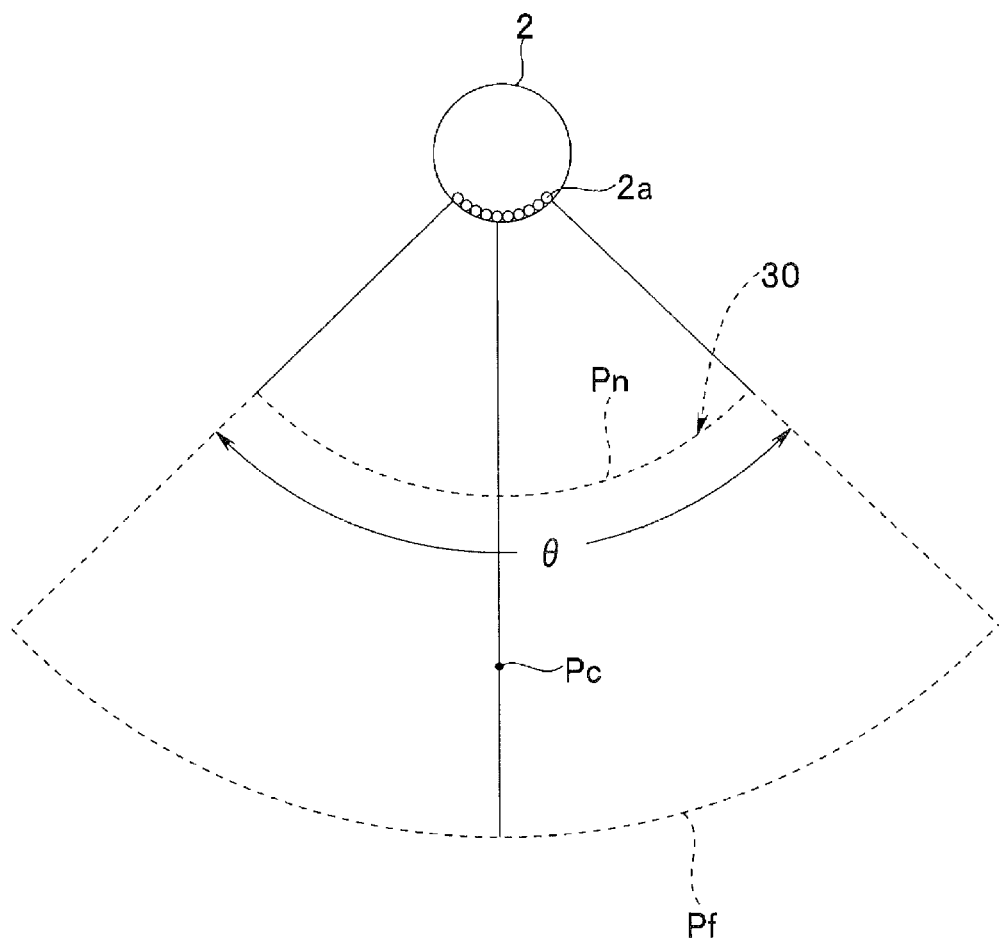
FIG. 4 is an explanatory diagram to illustrate the principle for changing the display region of an ROI with the ROI setup operation portion of FIG. 3.
Figure 5:
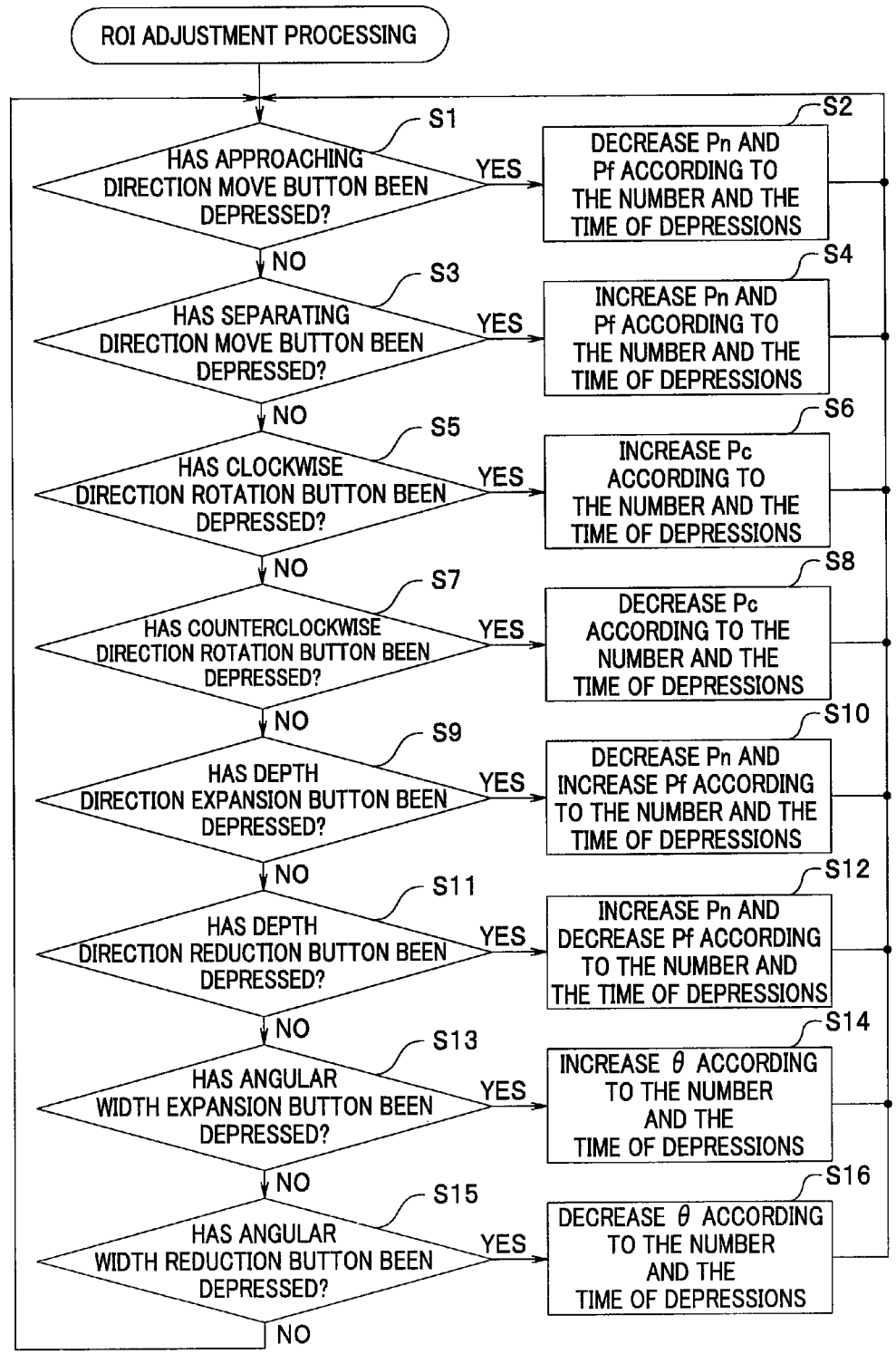
FIG. 5 is a flowchart showing the flow of the control processing of a CPU in the ultrasound diagnostic apparatus in FIG. 1.
Figure 6:
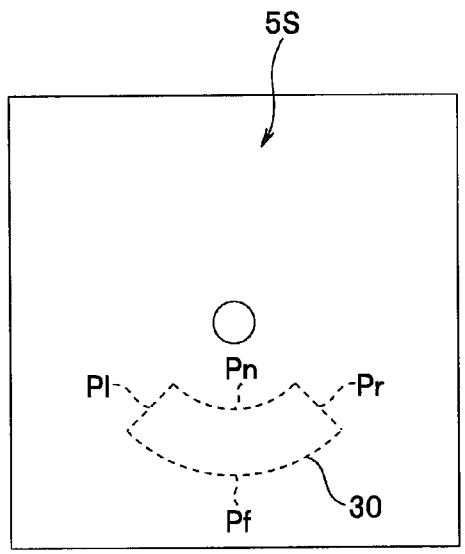
FIG. 6 is a screen display diagram showing a state in which an ROI in its initial state, which is an index image, is displayed on a monitor.

FIGS. 1 to 14 relate to an embodiment of the present invention, in which FIG. 1 is a block diagram showing an overall configuration of an ultrasound diagnostic apparatus using an index image control apparatus; FIG. 2 is a configuration diagram showing a specific configuration of the operation portion of FIG. 1; FIG. 3 is a diagram showing a configuration example of an ROI setup operation portion displayed on an LCD panel of FIG. 2; FIG. 4 is an explanatory diagram to illustrate the principle for changing the display region of an ROI with an ROI setup operation portion of FIG. 3; FIG. 5 is a flowchart showing the flow of the control processing of a CPU in the ultrasound diagnostic apparatus in FIG. 1; FIG. 6 is a screen display diagram showing a state in which an ROI in its initial state, which is an index image, is displayed on a monitor; and FIGS. 7 to 14 are screen display diagrams of a monitor for illustrating the action of the ultrasound diagnostic apparatus of the present embodiment.

As shown in FIG. 1, an ultrasound diagnostic apparatus 1 that uses an index image control apparatus of the present embodiment is configured to include an ultrasound probe 2, a processor 3, an operation portion 4 as operation means, and a monitor 5.

The ultrasound probe 2 is configured by arranging a plurality of ultrasound transducers 2a (hereafter, may be referred to as elements). The plurality of ultrasound transducers 2a are electrically connected to the processor 3 via a signal line.

It is noted that the ultrasound probe 2 used herein is of an electronic scanning type, in which the plurality of ultrasound transducers 2a are electronically driven to scan inside a body cavity (see FIG. 4). Since the specific configuration of the electronic scanning type ultrasound probe 2 is similar to that of existing electronic scanning type ultrasound probes, description thereof will be omitted.

The processor 3 can be detachably connected with the ultrasound probe 2. The processor 3 obtains an echo signal from the ultrasound probe 2 to generate an ultrasound image, and causes the generated ultrasound image to be displayed on the monitor 5.

Moreover, the processor 3 includes index image display means 7 that displays an ROI, which is an index image having a predetermined shape, on the monitor 5.

Now, a specific configuration of the processor 3 will be described.

As shown in FIG. 1, the processor 3 is principally made up of a transmission/reception section 6, a combining processing section 7A and an image processing section 7B that make up the index image display means 7 as an index image display section, a CPU 8 that makes up index image changing means as an index image changing section, and a memory 9.

The transmission/reception section 6 generates an electric transmission signal to drive an ultrasound transducer 2a (see FIG. 4) at the time of transmission, and outputs the signal to the corresponding ultrasound transducer 2a. The ultrasound transducer 2a converts the supplied electric transmission signal into ultrasound with each transducer, and transmits the ultrasound to a subject not shown.

Then, the ultrasound that is reflected at the subject is converted again into an electric signal by each oscillation element of the ultrasound transducer 2a, and the converted electrical signal is inputted to the transmission/reception section 6.

It is noted that the transmission/reception section 6 is adapted to select the ultrasound transducer 2a to be driven from among the plurality of ultrasound transducers 2a of the ultrasound probe 2 through the control by the CPU 8.

Moreover, the transmission/reception section 6 phases and adds the received signals from each ultrasound transducer 2a such that ultrasound is converged by using a block made up of, for example, an amplifier, a BPF, a LPF, and the like at the time of reception. Thereafter, the transmission/reception section 6 amplifies and converts the signal into digital data and thereafter outputs the signal to the combining processing section 7A.

The combining processing section 7A performs signal processing according to the type of digital data to be inputted. For example, in the case of a B-mode, the combining processing section 7A performs the processing to generate B-mode data, such as band-pass filtering, Log compression, wave detection, gain adjustment, and contrast adjustment.

Moreover, in the case of a color flow mode, the combining processing section 7A performs the processing to generate color data relating to blood flow.

In this case, the combining processing section 7A combines the color data according to the display region of an ROI and B-mode data to generate combined data, and outputs the generated combined data to the image processing section 7B.

The image processing section 7B performs image processing on the combined data from the combining processing section 7A to generate digital ultrasound data for image display, and thereafter converts the digital data into an analog image signal to output the same to the monitor 5 causing the ultrasound image based on the analog image signal to be displayed on the monitor 5, through the control by the CPU 8.

Next, the configuration of the operation portion 4 will be described by using FIGS. 1 to 3.

As shown in FIG. 1, the operation portion 4, which makes up index image operation means as an index image operation portion, is electrically connected to the CPU 8 of the processor 3. It is noted that the operation portion 4 and the CPU 8 may be connected through wired communication such as a connection cable, etc., or through wireless communication.

In the present embodiment, the operation portion 4 is configured to include a plurality of operation buttons that each simultaneously display both graphic information having a shape of an ROI in its initial state displayed on the monitor 5, and change information of at least one of upper, lower, leftward, and rightward directions for changing the display region of the ROI displayed on the monitor 5.

To be specific, the operation portion 4 is configured to include a CPU 12, a memory 13 that stores an execution program of the operation portion 4, a screen display control section 14, an LCD panel 15 that makes up a change information display section and can display the plurality of buttons, a key operation portion 16, a trackball 17, a switch group 18, and a memory 19 that stores display data for the LCD panel 15.

FIG. 2 shows an example of the arrangement of the LCD panel 15, the key operation portion 16, the trackball 17, and the switch group 18 in the operation portion 4.

As shown in FIG. 2, for example, the operation portion is arranged such that the key operation portion 16 made up of a plurality of keys and the LCD panel 15 are provided side by side as principal parts, and the trackball 17 is disposed in the middle of the area below the key operation portion 16 and the LCD panel 15, and three switch operation portions 18a, 18b, and 18c that make up the switch group 18 are disposed so as to interpose the trackball 17.

In the switch group 18, the switch operation portions 18a and 18b are switches for performing on/off operation of various settings, or increasing/decreasing the levels of various settings. Moreover, the switch operation portion 18c is made up of arrow operation keys of upper, lower, leftward, and rightward, and makes up other operation portion to be used, for example, when changing the display region of an ROI.

Therefore, the operation portion 4 is configured such that various operation switches are disposed in a layout that is easy to use for the operator.

It is noted that the operation portion 4 is not limited to the configuration as shown in FIG. 2, and the number of switches may be increased or decreased as needed, and the layout of the switches may be changed.

In the present embodiment, the LCD panel 15 of the operation portion 4 displays, for example, an operation panel screen 20 that makes up an ROI setup operation portion for setting up an ROI.

The operation panel screen 20 is displayed with an ROI position adjustment button 15A for adjusting the position of ROI, an ROI size change button 15B for adjusting the size of ROI, a flow gain adjustment button 15C for adjusting the gain of the blood flow image displayed in an ROI, a flow resolution button 15D for setting the resolution of the blood flow image in an ROI, and an ROI reset button 15E for performing a reset operation to return the display region of an ROI, which has been changed by the ROI position adjustment button 15A or the ROI size change button 15B, to its initial state.

It is noted that the LCD panel 15 is a touch panel, and depressing any of various buttons of the operation panel screen 20 will cause an operation signal corresponding to the depressed button to be outputted to the CPU 12.

Here, specific configurations of the ROI position adjustment button 15A and the ROI size change button 15B, which are part of principal parts of the present embodiment, will be described.

As shown in FIG. 3, the ROI position adjustment button 15A is configured to include an approaching direction move button 15a for moving the ROI closer toward the ultrasound transducer 2a, a separating direction move button 15b for moving the ROI in the direction separating from the ultrasound transducer 2a, a clockwise direction rotation button 15c for moving the ROI in the clockwise direction, and a counterclockwise direction rotation button 15d for moving the ROI in the counterclockwise direction.

Moreover, as shown in FIG. 3, the ROI size change button 15B is configured to include a depth direction reduction button 15e for reducing the size of the ROI in the depth direction, a depth direction expansion button 15f for expanding the side of the ROI in the depth direction, an angular width reduction button 15g for reducing the angular width of the ROI, and an angular width expansion button 15h for expanding the angular width of the ROI.

These buttons 15a to 15h each simultaneously displays both the shape of an ROI in its initial state, which is graphic information, and an arrow 21 that is change information and indicates an up/down and left/right direction in which the display region of the ROI is changed, thereby making up a plurality of operation buttons. Here, the shape of an ROI is displayed in a fan shape.

Moreover, the memory 19 stores display data for displaying an operation panel screen 20 including a plurality of buttons 15a to 15h of the above-described display configuration on the LCD panel 15, and the screen display control section 14 causes the operation panel screen 20 to be displayed on the LCD panel 14 by using the display data.

It is noted that in the present embodiment, the memory 19 also stores display data according to other plurality of operation panel screens, and through the control by the CPU 12, the screen display control section 14 can successively change and cause the operation panel screens of various settings to be displayed on the LCD panel 15, and also simultaneously perform the control to cause a plurality of operation buttons according to the displayed operation panel screen to be displayed.

Therefore, as a result of being provided with the ROI position adjustment button 15A and the ROI size change button 15B of the above-described configuration, the operation portion 4 is displayed with the shape of an ROI in its initial state and an arrow 21 according to the content of changing operations of the ROI, thus making it possible to intuitively select a button based on a desired operation content when perforating a changing operation of the display region of the ROI.

Then, upon depression of the ROI position adjustment button 15A and the ROI size change button 15B, an operation signal according to the depressed button is generated and outputted to the CPU 12.

It is noted that the switch operation portion 18c and the trackball 17 may be used to perform the operation to change the display region of ROI. In this case as well, upon operation of the operation portion 18c and the trackball 17, an operation signal according to an operation content is outputted to the CPU 12.

The CPU 12 outputs an operation signal relating to the operation of the LCD panel 15, the key operation portion 16, the trackball 17, or the switch group 18, to the CPU 8 of the processor 3.

It is noted that in the present embodiment, the memory 13 in the operation portion 4 stores a program for updating the display data and programs stored in the memory 19, and the like.

In this case, the CPU 8 of the processor 3 takes in an updating program from an external memory 10, and transmits the program to the operation portion 4 side. Then, the CPU 12 of the operation portion 4 writes the updating program and the display data, etc. into the memory 19.

In the present embodiment, the CPU 8 and the memory 9 in the processor 3 of FIG. 1 make up display form changing means as a display form changing section, and index image changing means.

The CPU 8 performs the control to change the display region of an ROI to be displayed on the monitor 5 according to the information of arrow 21 regarding each operation button 15a to 15h of the ROI position adjustment button 15A and the ROI size change button 15B in the operation portion 4.

Here, in order to display an ROI in its initial state on the monitor 5 with the index image display means 7 of the processor 3, and to change the display region of the ROI based on the operation of the operation portion 4, display data relating to the display of the ROI is needed.

In the present embodiment, the display data relating to the display of ROI is stored in the memory 9. The display data relating to the display of ROI will be described by using FIG. 4.

FIG. 4 shows the display data necessary for displaying an ROI in its initial state. As shown in FIG. 4, an ROI 30 in its initial state is displayed on the display screen of the monitor 5 that displays an ultrasound image, during the execution of a color flow mode.

In this case, in order to display an ROI 30 in its initial state on the monitor, the following display data are needed: display data Pn that indicate the display position closest from the ultrasound transducer 2a of the ultrasound probe 2, display data Pf that indicate the display position farthest from the ultrasound transducer 2a, display data Pc that indicates an angle at a middle position between the display data Pn and the display data Pf, and display angle width data θ that indicates the display angle width of the ROI 30.

For that reason, these display data are stored in the memory 9 as the initial state data of the ROI 30.

Then, the CPU 8 changes the display region of the ROI 30 based on the operation signal of the operation portion 4 by reading out the display data stored in the memory 9 and controlling the combining processing section by using the read-out display data.

It is noted that in this case, the CPU 8 performs the control to achieve a preset set value corresponding to one operation, when moving the ROI 30 in either direction of up/down direction and left/right direction, and expanding and reducing the size of the ROI 30 in either direction of up/down direction and left/right direction.

Next, the action of the ultrasound diagnostic apparatus of the present embodiment will be described by using FIGS. 5 to 14.

Figure 7:
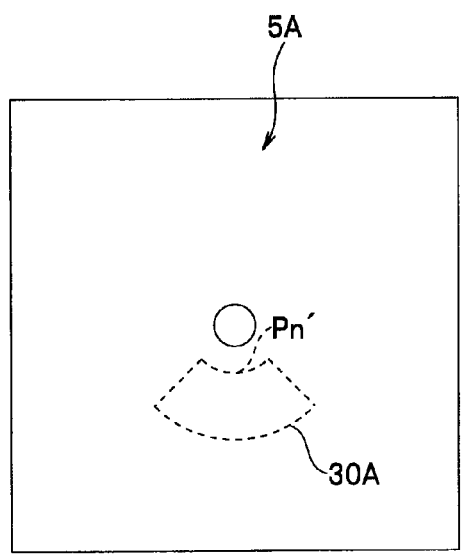
FIG. 7 is a screen display diagram showing a state in which an ROI has been moved from its initial state to a near point position on an ultrasound transducer side by the depression of an approaching direction move button.
Figure 8:
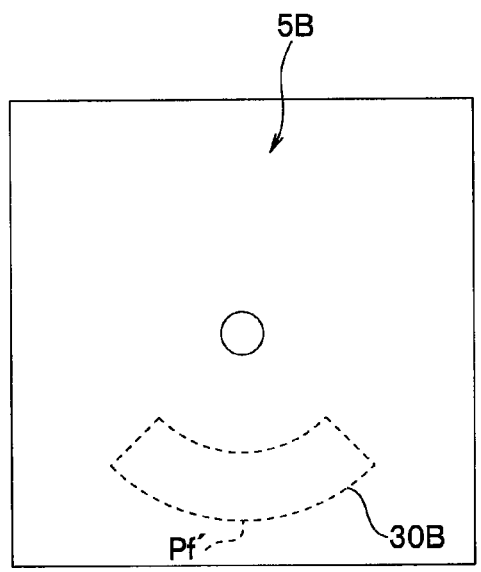
FIG. 8 is a screen display diagram showing a state in which an ROI has been moved from its initial state to a far point position on an ultrasound transducer side by the depression of a separating direction move button.
Figure 9:
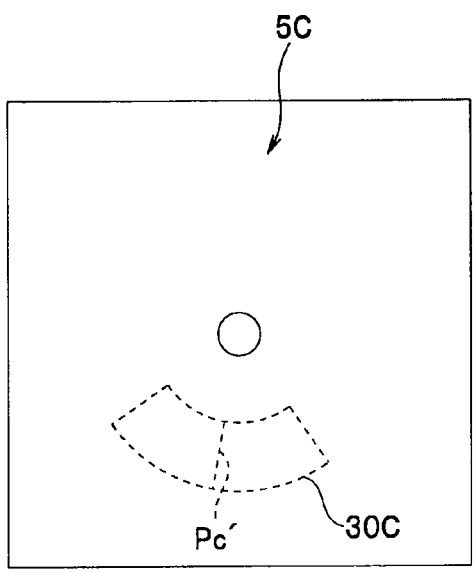
FIG. 9 is a screen display diagram showing a state in which an ROI has been moved in a clockwise direction from its initial state by the depression of a clockwise direction rotation button.
Figure 10:
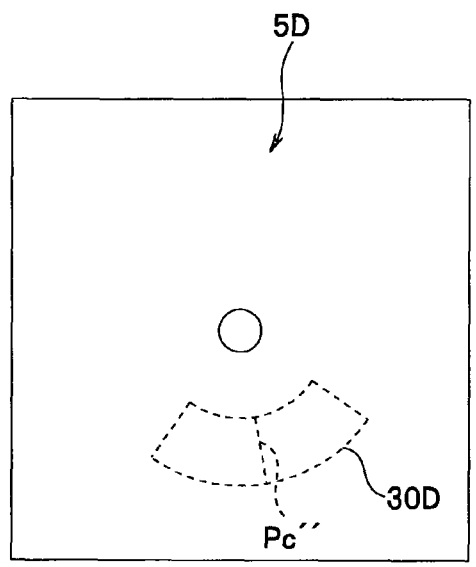
FIG. 10 is a screen display diagram showing a state in which an ROI has been moved in a counterclockwise direction from its initial state by the depression of a counterclockwise direction rotation button.
Figure 11:
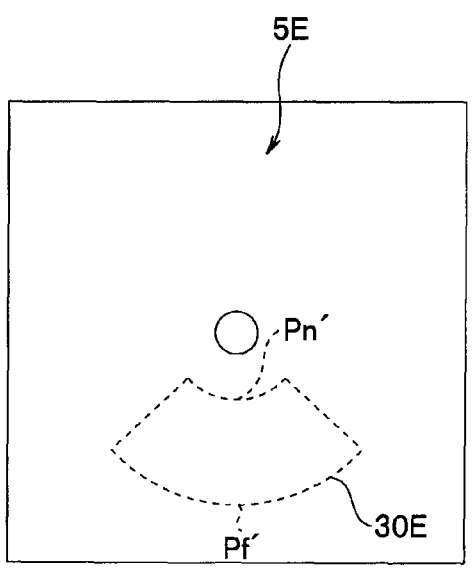
FIG. 11 is a screen display diagram showing a state in which an ROI has been expanded in the depth direction from its initial state by the depression of a depth-direction expansion button.
Figure 12:
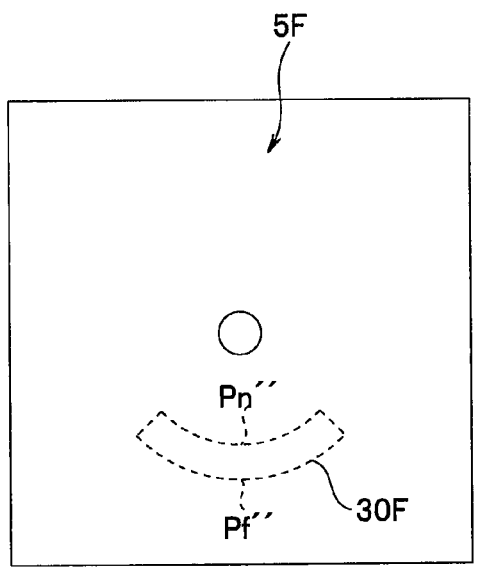
FIG. 12 is a screen display diagram showing a state in which an ROI is reduced in the depth direction from its initial state by the depression of a depth-direction reduction button.
Figure 13:
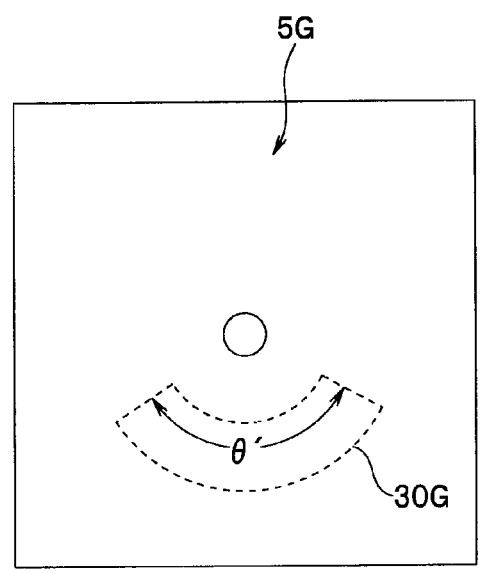
FIG. 13 is a screen display diagram showing a state in which the angle of an ROI has been expanded from its initial state by the depression of an angular width expansion button.
Figure 14:
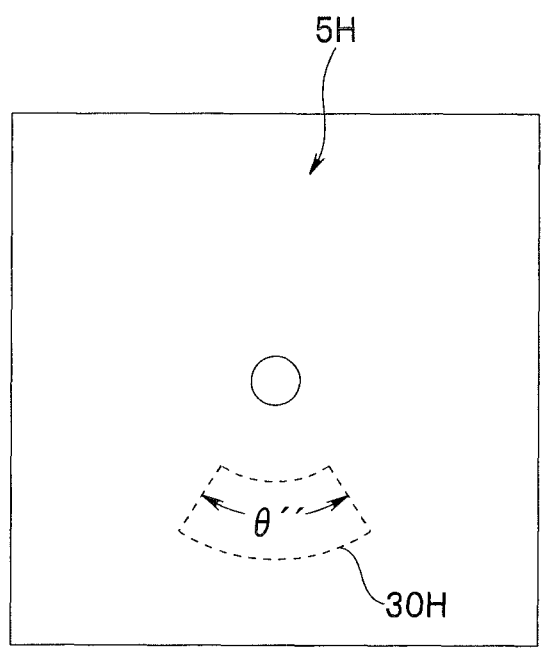
FIG. 14 is a screen display diagram showing a state in which the angle of an ROI is reduced from its initial state by the depression of an angular width reduction button.

It is noted that FIG. 5 is a flowchart showing the flow of the control processing of a CPU of the processor 3; FIG. 6 is a screen display diagram showing a state in which an ROI in its initial state, which is an index image, is displayed on a monitor; FIG. 7 is a screen display diagram showing a state in which an ROI has been moved from its initial state to a near point position on an ultrasound transducer side by the depression of an approaching direction move button; FIG. 8 is a screen display diagram showing a state in which an ROI has been moved from its initial state to a far point position on an ultrasound transducer side by the depression of a separating direction move button; FIG. 9 is a screen display diagram showing a state in which an ROI has been moved in a clockwise direction from its initial state by the depression of a clockwise direction rotation button; FIG. 10 is a screen display diagram showing a state in which an ROI has been moved in a counterclockwise direction from its initial state by the depression of a counterclockwise direction rotation button; FIG. 11 is a screen display diagram showing a state in which an ROI has been expanded in the depth direction from its initial state by the depression of a depth-direction expansion button; FIG. 12 is a screen display diagram showing a state in which an ROI is reduced in the depth direction from its initial state by the depression of a depth-direction reduction button; FIG. 13 is a screen display diagram showing a state in which the angle of an ROI has been expanded from its initial state by the depression of an angular width expansion button; and FIG. 14 is a screen display diagram showing a state in which the angle of an ROI is reduced from its initial state by the depression of an angular width reduction button.

Now, suppose that an operator changes the display region of the ROI 30 displayed on the monitor 5 by using the ultrasound diagnostic apparatus 1 shown in FIG. 1. In this case, the CPU 8 of FIG. 1 reads out and executes the program that performs ROI adjustment processing shown in FIG. 5 and stored in the memory 9.

The CPU 8 determines whether or not the approaching direction move button 15a has been depressed in the judgment processing of step S1. Then, when the button has not been depressed, the CPU 8 moves the process to step S3, and when the button has been depressed, the CPU 8 controls the index image display means 7 so as to reduce the display data Pn and Pf shown in FIG. 4 according to the number and the time of button depressions in the processing of step S2, thereafter returning the process to step S1.

By this processing of step S2, for example, display screen 5A shown in FIG. 7 is displayed on the monitor 5, and the display screen 5A displays an ROI 30A that indicates the ROI 30 having moved to a near point position Pn' on the ultrasound transducer side from the position of the initial state shown in FIG. 6.

Thereafter, the CPU 8 determines whether or not the separating direction move button 15b is depressed in the judgment processing of step S3. Then, when the button has not been depressed, the CPU 8 moves the process to step S5, and when the button has been depressed, controls the index image display means 7 so as to increase the display data Pn and Pf shown in FIG. 4 according to the number and the time of button depressions in the processing of step S4, thereafter returning the process to step S1.

By the processing of step S4, for example, a display screen 5B shown in FIG. 8 is displayed on the monitor 5, and the display screen 5B displays an ROI 30B that indicates the ROI 30 having moved to a far point position Pf' on the ultrasound transducer side from the position of the initial state shown in FIG. 6.

Next, the CPU 8 determines whether or not the clockwise direction rotation button 15c has been depressed in the judgment processing of step S5. Then, when the button has not been depressed, the CPU 8 moves the process to step S7, and when the button has been depressed, controls the index image display means 7 so as to increase the display data Pc shown in FIG. 4 according to the number and the time of button depressions in the processing of step S6, thereafter returning the process to step S1.

By the processing of step S6, for example, a display screen 5C shown in FIG. 9 is displayed on the monitor 5, and the display screen 5C displays an ROI 30C that indicates the ROI 30 having rotated and moved to a position Pc' in the clockwise direction from the position of the initial state shown in FIG. 6.

Thereafter, the CPU 8 determines whether or not the counterclockwise direction rotation button 15d has been depressed in the judgment processing of step S7. Then, when the button has not been depressed, the CPU 8 moves the process to step S9, and when the button has been depressed, controls the index image display means 7 so as to decrease the display data Pc shown in FIG. 4 according to the number and the time of button depressions in the processing of step S8, thereafter returning the process to step S1.

By this processing of step S8, for example, a display screen 5C shown in FIG. 10 is displayed on the monitor 5, and the display screen 5C displays an ROI 30D that indicates the ROI 30 having rotated and moved to a position Pc" in the counterclockwise direction from the position of the initial state shown in FIG. 6.

Next, the CPU 8 determines whether or not the depth direction expansion button 15f has been depressed in the judgment processing of step S9. Then, when the button has not been depressed, the CPU 8 moves the process of step S11, and when the button has been depressed, controls the index image display means 7 so as to decrease the display data Pn and increase the display data Pf shown in FIG. 4 according to the number and the time of button depressions in the processing of step S10, thereafter returning the process to step S1.

By this processing of step S10, for example, a display screen 5E shown in FIG. 11 is displayed on the monitor 5, and the display screen 5E displays an ROI 30E that indicates the ROI 30 whose display region has been expanded between a near point position Pn' and a far point position Pf' of the ultrasound transducer 2a from the position in the initial state shown in FIG. 6.

Thereafter, the CPU 8 determines whether or not the depth direction reduction button 15e is depressed in the judgment processing of step S11. Then, when the button has not been depressed, the CPU 8 moves the process to step S13, and when the button has been depressed, controls the index image display means 7 so as to increase the display data Pn and decrease the display data Pf shown in FIG. 4 according to the number and the time of button depressions in the processing of step S12, thereafter returning the process to step S1.

By this processing of step S12, for example, a display screen 5F shown in FIG. 12 is displayed on the monitor 5, and the display screen 5F displays an ROI 30F that indicates the ROI 30 whose display region has been reduced between a near point position Pn" and a far point position Pf" of the ultrasound transducer 2a from the position in the initial state shown in FIG. 6.

Next, the CPU 8 determines whether or not the angular width expansion button 15h has been depressed in the judgment processing of step S13. Then, when the button has not been depressed, the CPU 8 moves the process to step S15, and when the button has been depressed, controls the index image display means 7 so as to increase the display angular data θ shown in FIG. 4 according to the number and the time of button depressions in the processing of step S14, thereafter returning the process to step S1.

By this processing of step S14, for example, display screen 5G shown in FIG. 13 is displayed on the monitor 5, and the display screen 5G displays an ROI 30G that indicates the ROI 30 having being expanded to a display angle data θ' from the position of the initial state shown in FIG. 6.

Next, the CPU 8 determines whether or not the angular width reduction button 15g has been depressed in the judgment processing of step S15. Then, when the button has not been depressed, the CPU 8 returns the process to step S1, and when the button has been depressed, controls the index image display means 7 so as to decrease the display angular data θ shown in FIG. 4 according to the number and the time of button depressions in the processing of step S16, thereafter returning the process to step S1.

By this processing of step S16, for example, a display screen 5H shown in FIG. 14 is displayed on the monitor 5, and the display screen 5H displays an ROI 30H that indicates the ROI 30 having being reduced to a display angle data θ" from the position of the initial state shown in FIG. 6.

It is noted that such program based on an ROI adjustment processing by the CPU 8 will not be limited to the flowchart shown in FIG. 5, and for example, the order of judgment processing may be changed as needed such that the judgment processing of the depression or non depression of an operation button of a high usage frequency out of a plurality of operation buttons 15a to 15h is first performed.

Therefore, according to the present embodiment, owing to the button display that has a display of information by which operation content can be intuitively grasped, the display region of an ROI 30 displayed on the monitor 5 can be easily changed during the execution of a color flow mode, thereby improving the operability.

It is noted that although, in the present embodiment, description has been made on the case in which the display region of the ROI displayed on the display screen of the monitor of a full circle display mode during the execution of a color flow mode is changed, the present embodiment, of course, can be applied to the case in which the display region of ROI during a half circle display mode is changed.

The present invention will not be limited to the embodiments and the variant which have been described so far, and can be modified and practiced in various ways without departing from the spirit of the invention.

What is claimed is:

1. An index image control apparatus, comprising:
   an index image display section which is provided in an ultrasound diagnostic apparatus that generates an ultrasound image of a subject and displays a generated ultrasound image on a monitor, and which displays an index image having a predetermined shape and to be superimposed on an image displayed on the monitor;
   a display form changing section that can change a display form of the index image by a predetermined amount by one operation;
   an operation section for outputting an operation signal to the display form changing section; and
   a change information display section provided in the operation section and displaying a plurality of operation buttons each including graphic information that indicates an initial state of the index image, and change information that is changed by the display form changing section,
   wherein the index image having the predetermined shape is an image of a region of interest displayed on a display screen of the monitor on which the ultrasound image of the subject generated by the ultrasound diagnostic apparatus is displayed, when a flow mode is executed by the ultrasound diagnostic apparatus;
   the plurality of operation buttons are different from one another in the change information,
   the plurality of operation buttons includes: an approaching direction move button for moving the index image closer toward an ultrasound transducer on the ultrasound image; a separating direction move button for moving the index image in the direction separating from the ultrasound transducer on the ultrasound image; a clockwise direction rotation button for moving the index image in the clockwise direction on the ultrasound image; and a counterclockwise direction rotation button for moving the index image in the counterclockwise direction on the ultrasound image, and
   the display form changing section changes the display form of the index image by a predetermined amount by one operation for each operation button that is operated.

2. The index image control apparatus according to claim 1, wherein the plurality of operation buttons further include: a depth direction reduction button for reducing a size of the index image in the depth direction on the ultrasound image, a depth direction expansion button for expanding the size of the index image in the depth direction on the ultrasound image, an angular width reduction button for reducing an angular width of the index image on the ultrasound image, and an angular width expansion button for expanding the angular width of the index image on the ultrasound image.

3. The index image control apparatus according to claim 1, wherein the plurality of operation buttons are configured to be displayed in a screen of a touch panel.

4. The index image control apparatus according to claim 1, wherein the change information is displayed as an arrow in each of the plurality of operation buttons.

5. The index image control apparatus according to claim 1, wherein the graphic information is displayed in a fan shape in each of the plurality of operation buttons.

6. An index image control apparatus, comprising:
  an index image display section for displaying an index image having a predetermined shape on a monitor;
  an index image operation section including a plurality of operation buttons that each simultaneously display both graphic information having a shape in an initial state of the index image displayed on the monitor, and change information; and
  an index image changing section for changing a display region of the index image displayed on the monitor according to the change information on an operation button that is operated in the index image operation section,
  wherein the index image having the predetermined shape is an image of a region of interest displayed on a display screen of the monitor on which the ultrasound image of the subject generated by the ultrasound diagnostic apparatus is displayed, when a flow mode is executed by the ultrasound diagnostic apparatus,
  the change information indicates at least one of upper, lower, leftward, and rightward directions in which the display region of the index image displayed on the monitor is changed, and
  the index image changing section changes the display region of the index image by a predetermined amount by one operation of the operation button that is operated.

7. The index image control apparatus according to claim 6, wherein the index image changing section changes a display region of the index image by moving the index image on a display screen of the monitor, or by expanding or reducing a size of the index image according to the change information on the operation button that is operated.

8. The index image control apparatus according to claim 7, wherein moving of the index image, and expansion and reduction of the size of the index image are performed by the predetermined amount for one operation to the operation button that is operated.

9. The index image control apparatus according to claim 6, wherein the plurality of operation buttons are configured to be displayed in a screen of a touch panel.

10. The index image control apparatus according to claim 9, wherein the change information is displayed as an arrow on each operation button.

11. The index image control apparatus according to claim 9, wherein the graphic information is displayed as a fan shape on each operation button.

12. The index image control apparatus according to claim 6, wherein the change information is displayed as an arrow on each operation button.

13. The index image control apparatus according to claim 6, wherein the graphic information is displayed as a fan shape on each operation button.

* * * * *